US010765832B2

(12) United States Patent
Brustad et al.

(10) Patent No.: US 10,765,832 B2
(45) Date of Patent: Sep. 8, 2020

(54) MEDICAL TUBING HAVING VARIABLE CHARACTERISTICS AND METHOD OF MAKING SAME

(71) Applicant: Applied Medical Resources Corporation, Rancho Santa Margarita, CA (US)

(72) Inventors: John R. Brustad, Rancho Santa Margarita, CA (US); Said S. Hilal, Rancho Santa Margarita, CA (US); Nabil Hilal, Rancho Santa Margarita, CA (US); Charles C. Hart, Rancho Santa Margarita, CA (US); Gary M. Johnson, Rancho Santa Margarita, CA (US); Serene Wachli, Rancho Santa Margarita, CA (US); Ghassan Sakakine, Rancho Santa Margarita, CA (US); Donald L. Gadberry, Capistrano Beach, CA (US); Edward D. Pingleton, San Juan Capistrano, CA (US); Matthew N. Petrime, Rancho Santa Margarita, CA (US); Payam Adlparvar, Lake Forest, CA (US); Carl B. Hadley, Rancho Santa Margarita, CA (US); Kenneth K. Vu, San Diego, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 15/949,443

(22) Filed: Apr. 10, 2018

(65) Prior Publication Data

US 2018/0221623 A1    Aug. 9, 2018

Related U.S. Application Data

(60) Continuation of application No. 14/223,032, filed on Mar. 24, 2014, now Pat. No. 9,987,460, which is a
(Continued)

(51) Int. Cl.
*A61M 25/02* (2006.01)
*A61M 25/00* (2006.01)
(Continued)

(52) U.S. Cl.
CPC ....... *A61M 25/0012* (2013.01); *A61B 1/0011* (2013.01); *A61B 1/0055* (2013.01);
(Continued)

(58) Field of Classification Search
CPC ............ A61M 25/0012; A61M 25/005; A61M 25/0034; A61M 2025/0034;
(Continued)

(56) References Cited

U.S. PATENT DOCUMENTS 2,130,586 A    9/1938  Huston
2,688,329 A    9/1954  Wallace
(Continued)

FOREIGN PATENT DOCUMENTS

EP    0 421 650 A    4/1991
EP    0 605 796 A2   7/1994
(Continued)

OTHER PUBLICATIONS

International Searching Authority, Patent Cooperation Treaty PCT International Search Report and Written Opinion for International Application No. PCT/US205/001129, dated Nov. 23, 2005, 20 pages.
(Continued)

*Primary Examiner* — Scott W Dodds
(74) *Attorney, Agent, or Firm* — Patrick Ikehara

(57) ABSTRACT

The invention primarily is directed to a medical tubing adapted for insertion into a body tissue or cavity and method of manufacturing different variations of the tubing along a length of the tubing. The tubing comprises a plurality of individual, discrete, generally ring-shaped elements arranged in series and fused or bonded together forming a continuous tubular structure. The ring-shaped elements may
(Continued)

include a combination of flexible and rigid ring-shaped elements assembled along different portions or sections of the tubular structure. In another aspect of the invention, the medical tubing may further comprise a secondary lumen and a pull wire to control the tubular structure. In another aspect of the invention, the ring-shaped elements may vary in diameter and/or composition in different portions or sections of the tubular structure.

11 Claims, 4 Drawing Sheets

Related U.S. Application Data continuation of application No. 12/877,245, filed on Sep. 8, 2010, now Pat. No. 8,715,441, which is a division of application No. 10/766,138, filed on Jan. 28, 2004, now abandoned.

(51) Int. Cl.
  *A61B 1/005*  (2006.01)
  *A61B 17/34*  (2006.01)
  *A61B 1/00*  (2006.01)
  *A61B 17/00*  (2006.01)
  *A61M 39/08*  (2006.01)

(52) U.S. Cl.
  CPC ..... *A61B 17/3421* (2013.01); *A61M 25/0043* (2013.01); *A61B 2017/003* (2013.01); *A61M 2025/0034* (2013.01); *A61M 2025/0037* (2013.01); *A61M 2039/082* (2013.01)

(58) Field of Classification Search
  CPC .... A61M 2025/0037; A61M 2039/082; B29C 53/562; B29C 53/566; B29C 53/58; B29C 53/583; B29C 53/60
  See application file for complete search history.

(56) References Cited

U.S. PATENT DOCUMENTS

| | | |
|---|---|---|
| 2,688,343 A | 9/1954 | Cuddeback |
| 2,701,562 A | 2/1955 | Michael et al. |
| 2,722,263 A | 11/1955 | Beare et al. |
| 3,113,897 A | 12/1963 | Gisle Skansen et al. |
| 3,226,767 A | 1/1966 | Howell |
| 3,354,695 A | 11/1967 | Szente |
| 3,477,891 A | 11/1969 | Hawerkamp |
| 3,503,385 A | 3/1970 | Stevens |
| 3,585,707 A | 6/1971 | Stevens |
| 3,617,415 A | 11/1971 | Hawerkamp |
| 3,618,613 A | 11/1971 | Schulte |
| 3,910,808 A | 10/1975 | Steward |
| 3,919,026 A | 11/1975 | Mizutani et al. |
| 3,988,190 A | 10/1976 | McWilliams |
| 4,010,054 A | 3/1977 | Bradt |
| 4,051,844 A | 10/1977 | Chiulli |
| 4,078,957 A | 3/1978 | Bradt |
| 4,135,869 A | 1/1979 | Loyer |
| 4,302,261 A | 11/1981 | Simkins et al. |
| 4,343,672 A | 8/1982 | Kanao |
| 4,350,547 A | 9/1982 | Kanao |
| 4,466,854 A | 8/1984 | Hawerkamp |
| 4,470,941 A | 9/1984 | Kurta |
| 4,540,360 A | 9/1985 | Leo |
| 4,586,923 A | 5/1986 | Gould et al. |
| 4,596,028 A | 5/1986 | Gould et al. |
| 4,605,990 A | 8/1986 | Wilder et al. |
| 4,619,643 A | 10/1986 | Bai et al. |
| 4,690,175 A | 9/1987 | Ouchi et al. |
| 4,707,906 A | 11/1987 | Posey |
| 4,811,743 A | 3/1989 | Stevens |
| 4,818,460 A | 4/1989 | Nied |
| 4,820,274 A | 4/1989 | Choksi et al. |
| 4,826,423 A | 5/1989 | Kemp et al. |
| 4,911,148 A | 3/1990 | Sosnowski |
| 5,084,033 A | 1/1992 | O'Neill |
| 5,092,950 A | 3/1992 | Spoo et al. |
| 5,179,935 A | 1/1993 | Miyagi |
| 5,180,376 A | 1/1993 | Fischell et al. |
| 5,195,968 A | 3/1993 | Lundquist et al. |
| 5,228,441 A | 7/1993 | Lundquist |
| 5,254,088 A | 10/1993 | Lundquist et al. |
| H1261 H | 12/1993 | Gibson et al. |
| 5,273,535 A | 12/1993 | Edwards et al. |
| 5,275,151 A | 1/1994 | Shockey et al. |
| 5,284,128 A | 2/1994 | Hart |
| 5,304,131 A | 4/1994 | Paskar |
| 5,305,740 A * | 4/1994 | Kolobow ............... A61M 16/04 128/207.14 |
| 5,315,996 A | 5/1994 | Lundquist |
| 5,322,064 A | 6/1994 | Lundquist |
| 5,328,467 A | 7/1994 | Edwards et al. |
| 5,329,923 A | 7/1994 | Lundquist |
| 5,342,299 A | 8/1994 | Snoke et al. |
| D351,652 S | 10/1994 | Thompson et al. |
| 5,383,852 A | 1/1995 | Stevens-Wright |
| 5,395,327 A | 3/1995 | Lundquist et al. |
| 5,409,469 A | 4/1995 | Schaerf |
| 5,429,127 A | 7/1995 | Kolobow |
| 5,441,483 A | 8/1995 | Avitall |
| 5,456,664 A | 10/1995 | Heinzelman et al. |
| 5,462,527 A | 10/1995 | Steven-Wright et al. |
| 5,472,435 A | 12/1995 | Sutton |
| 5,484,407 A | 1/1996 | Osypka |
| 5,507,751 A | 4/1996 | Goode |
| 5,509,408 A | 4/1996 | Kurtis |
| 5,509,910 A | 4/1996 | Lunn |
| 5,512,035 A | 4/1996 | Konstorum et al. |
| 5,531,687 A | 7/1996 | Snoke et al. |
| 5,531,721 A | 7/1996 | Pepin et al. |
| 5,558,737 A | 9/1996 | Brown et al. |
| 5,632,734 A | 5/1997 | Galel |
| 5,637,168 A | 6/1997 | Carlson |
| 5,702,433 A | 12/1997 | Taylor et al. |
| 5,709,665 A | 1/1998 | Vergano et al. |
| 5,774,950 A | 7/1998 | Stout |
| 5,792,116 A | 8/1998 | Berg et al. |
| 5,827,278 A | 10/1998 | Webster, Jr. |
| 5,836,925 A | 11/1998 | Soltesz et al. |
| 5,840,031 A | 11/1998 | Crowley |
| 5,848,986 A | 12/1998 | Lundquist et al. |
| 5,863,366 A | 1/1999 | Snow |
| 5,865,800 A | 2/1999 | Mirarchi et al. |
| 5,879,499 A | 3/1999 | Corvi |
| 5,888,436 A | 3/1999 | keith et al. |
| 5,891,088 A | 4/1999 | Thompson et al. |
| 5,902,287 A | 5/1999 | Martin |
| 5,904,667 A | 5/1999 | Falwell |
| 5,935,102 A | 8/1999 | Bowden et al. |
| 5,945,048 A | 8/1999 | Ensinger |
| 5,947,940 A | 9/1999 | Beisel et al. |
| 5,976,075 A | 11/1999 | Beane et al. |
| 5,984,907 A | 11/1999 | McGee et al. |
| 6,007,531 A | 12/1999 | Snoke et al. |
| 6,014,579 A | 1/2000 | Pomeranz et al. |
| 6,033,378 A | 3/2000 | Lindquist et al. |
| 6,045,547 A | 4/2000 | Ren |
| 6,146,355 A | 11/2000 | Biggs |
| 6,171,277 B1 | 1/2001 | Ponzi |
| 6,198,974 B1 | 3/2001 | Webster, Jr. |
| 6,203,732 B1 | 3/2001 | Clubb et al. |
| 6,246,914 B1 | 6/2001 | de la Rama |
| 6,263,224 B1 | 7/2001 | West |
| 6,306,235 B1 | 10/2001 | Henderson |
| 6,337,142 B2 | 1/2002 | Harder |
| 6,368,316 B1 | 4/2002 | Jansen et al. |
| 6,451,005 B1 | 9/2002 | Saitou et al. |
| 6,464,632 B1 | 10/2002 | Taylor |
| 6,485,455 B1 | 11/2002 | Thompson et al. |
| 6,500,167 B1 | 12/2002 | Webster, Jr. |

(56) References Cited

U.S. PATENT DOCUMENTS

| | | |
|---|---|---|
| 6,511,471 B2 | 1/2003 | Rosenman et al. |
| 6,533,770 B1 | 3/2003 | Lepulu et al. |
| 6,533,984 B2 | 3/2003 | Curti |
| 6,537,405 B1 | 3/2003 | Henderson et al. |
| 6,540,734 B1 | 4/2003 | Chiu et al. |
| 6,544,215 B1 | 4/2003 | Bencini et al. |
| 6,599,265 B2 | 7/2003 | Bon |
| 6,602,278 B1 | 8/2003 | Thompson et al. |
| 6,605,171 B1 | 8/2003 | Debalme et al. |
| 6,648,875 B2 | 11/2003 | Simpson et al. |
| 6,652,506 B2 | 11/2003 | Bowe et al. |
| 6,663,588 B2 | 12/2003 | DuBois et al. |
| 6,669,886 B1 | 12/2003 | Willard |
| 6,716,207 B2 | 4/2004 | Farnholtz |
| 6,776,765 B2 | 8/2004 | Soukup et al. |
| 6,783,491 B2 | 8/2004 | Saadat et al. |
| 6,804,866 B2 | 10/2004 | Lemke et al. |
| 6,836,687 B2 | 12/2004 | Kelley et al. |
| D504,175 S | 4/2005 | Westbrook |
| 6,916,306 B1 | 7/2005 | Jenkins et al. |
| 6,976,987 B2 | 12/2005 | Flores |
| 6,979,312 B2 | 12/2005 | Shimada |
| 7,005,026 B2 | 2/2006 | Brustad et al. |
| 7,534,317 B2 | 5/2009 | Brustad et al. |
| 7,850,811 B2 | 12/2010 | Hart et al. |
| 2001/0037084 A1 | 11/2001 | Nardeo |
| 2002/0022762 A1 | 2/2002 | Beane et al. |
| 2002/0177789 A1 | 11/2002 | Ferry et al. |
| 2003/0135199 A1 | 7/2003 | Rosenman et al. |
| 2003/0149422 A1 | 8/2003 | Muller |
| 2003/0163082 A1* | 8/2003 | Mertens ............ A61M 1/3653 604/43 |
| 2003/0163085 A1 | 8/2003 | Tanner et al. |
| 2003/0199817 A1 | 10/2003 | Thompson et al. |
| 2003/0201058 A1 | 10/2003 | Banas et al. |
| 2003/0230823 A1 | 12/2003 | Bartholomew |
| 2003/0236493 A1 | 12/2003 | Mauch |
| 2004/0010243 A1 | 1/2004 | Klint |
| 2004/0215109 A1 | 10/2004 | Pingleton et al. |
| 2005/0096590 A1 | 5/2005 | Gullickson et al. |
| 2005/0131387 A1 | 6/2005 | Pursley |
| 2005/0159728 A1 | 7/2005 | Armour et al. |
| 2005/0165366 A1 | 7/2005 | Brustad |
| 2005/0197623 A1 | 9/2005 | Leeflang et al. |
| 2005/0277851 A1 | 12/2005 | Whittaker et al. |
| 2005/0277875 A1 | 12/2005 | Selkee |
| 2005/0288627 A1 | 12/2005 | Mogul |
| 2005/0288656 A1 | 12/2005 | Koerner et al. |
| 2007/0215268 A1 | 9/2007 | Pingleton et al. |
| 2007/0277921 A1 | 12/2007 | Hart et al. |
| 2011/0066105 A1 | 3/2011 | Hart et al. |

FOREIGN PATENT DOCUMENTS

| | | |
|---|---|---|
| JP | 405038325 A | 2/1993 |
| WO | WO 97/10749 A | 3/1997 |
| WO | WO 00/25849 A | 5/2000 |
| WO | WO 03/015638 A | 2/2003 |

OTHER PUBLICATIONS

European Patent Office, Supplementary European Search Report for Application No. EP 04 75 0825, based on International Application No. PCT/US2004/013118, dated Oct. 2, 2006.

International Searching Authority, International Search Report and Written Opinion for PCT/US04/13118, dated Mar. 8, 2006.

The International Bureau of WIPO, International Preliminary Report on Patentability for International Application No. PCT/US/2004/013118, dated Mar. 27, 2006, entitled Steer.

International Searching Authority, International Search Report and Written Opinion for PCT/US07/069282 dated Jan. 16, 2008.

The International Bureau of WIPO, International Preliminary Report on Patentability for International Application No. PCT/US/2007/069282, dated Nov. 18, 2008.

International Bureau of WIPO, International Preliminary Report on Patentability for International Application No. PCT/US/2005/001129 dated Jul. 31, 2006.

* cited by examiner

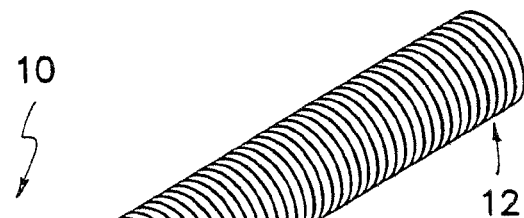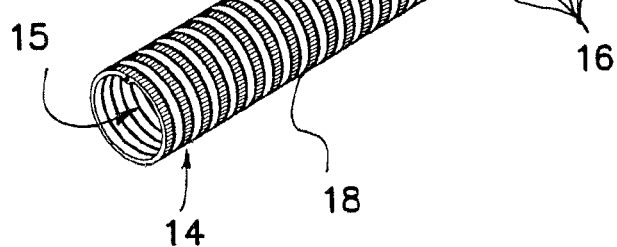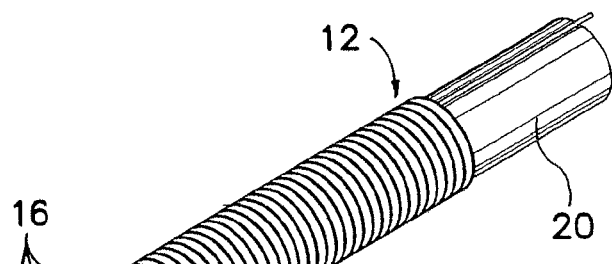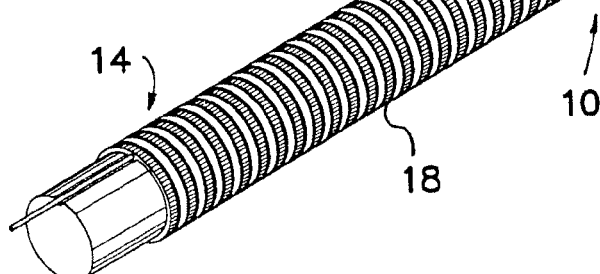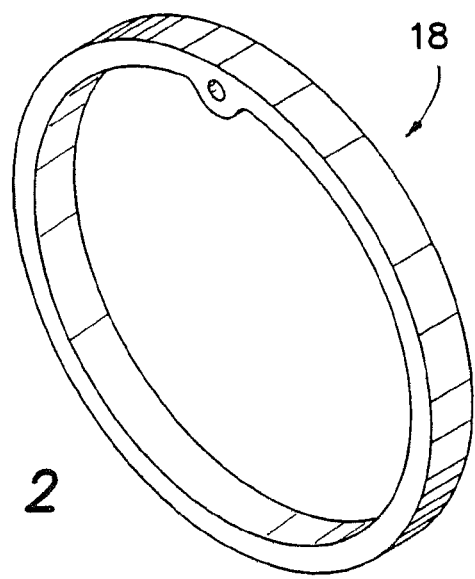

MEDICAL TUBING HAVING VARIABLE CHARACTERISTICS AND METHOD OF MAKING SAME

CROSS-REFERENCE TO RELATED APPLICATIONS

This application is a continuation of U.S. patent application Ser. No. 14/223,032 entitled "Medical tubing having variable characteristics and method of making same" filed on Mar. 24, 2014 which is a continuation of U.S. patent application Ser. No. 12/877,245 now U.S. Pat. No. 8,715,441 issued May 6, 2014 entitled "Medical tubing having variable characteristics and method of making same" filed on Sep. 8, 2010 which is a divisional of U.S. patent application Ser. No. 10/766,138 filed on Jan. 28, 2004 entitled "Medical tubing having variable characteristics and method of making same" the disclosures of all of which are hereby incorporated by reference in their entireties as if fully set forth herein.

BACKGROUND OF THE INVENTION

Field of the Invention

This invention generally relates to medical devices and, more specifically, to medical tubing adapted for insertion into a body tissue or cavity having variable characteristics and method of making same.

Discussion of Related Art

Medical tubing includes tubing used as catheters, drain tubes, access ports, endoscope bodies and the like. The requirements for each type of medical tubing will depend on its use. In particular, a specific length of medical tubing may vary depending on each application. For example, a specific length of medical tubing may need to be very flexible and yet pushable, or it may need to be thin-walled and yet kink-resistant. In addition, the tubing may need to exhibit these properties in only specific regions.

Most medical tubing is extruded from a single plastic material in a continuous forming process. Certain characteristics or variations may be imparted to the extruded tubing by altering the speed or the tension of the extruded material as it exits and cools from the extrusion machine. However, the variations are limited by the fact that a single material is extruded. Recent advances in extrusion technology have allowed the co-extrusion of multiple materials. This provides some usable variations in extruded tubing. Nevertheless, this is still a linear process and is still limited by the continuous flow of the extruded materials.

Accordingly, there is a need for a medical tubing having a length with variable characteristics and a method of making the tubing such that variations can occur along the length of the manufactured tubing. For instance, a length of the tubing may be rigid for a length, becomes flexible for a length and then becomes rigid again for another length. It is also desirable to have large variations in the diameter of the tubing. In another application, there may be a need for a tube that is extremely kink-resistant in a specific region. Kink-resistance with very thin walls is not obtainable through the current extrusion processes.

SUMMARY OF THE INVENTION

The invention is primarily directed to a medical tubing adapted for insertion into a body tissue or cavity and method of manufacturing different variations of the tubing along a length of the tubing. In one aspect of the invention, the medical so tubing includes a length with variable characteristics, the tubing comprising a plurality of individual, discrete, generally ring-shaped elements arranged in series and fused or bonded together forming a continuous tubular structure. The ring-shaped elements may be formed of a thermoplastic or a thermoset material. The ring-shaped elements may include plastic rings, metallic rings, un-reinforced plastic rings and/or metal reinforced plastic rings assembled along the length of the tubular structure to provide variable flexibility and kink-resistance. The tubular structure may be bent, twisted or curved without kinking. The tubular structure may have a cross-section that is circular, oval, rectangular, triangular, hexagonal or any geometric shape. The ring-shaped elements may have different flexural modulus. The ring-shaped elements may include a combination of flexible and rigid ring-shaped elements assembled along different portions or sections of the tubular structure, wherein as the tubular structure is bent, twisted or curved, the rigid ring-shaped elements provide reinforcement to maintain the size and shape of the lumen and the flexible ring-shaped elements operate to stretch and compress to prevent kinking. The ring-shaped elements may be metallic and may be bonded with a resilient, flexible elastomeric adhesive, wherein the ring-shaped elements may have different lengths and may be fused closer or further apart to one another depending on the characteristics of a portion or section of the tubing.

In another aspect of the invention, the medical tubing may further comprise a secondary lumen and a pull wire to control the tubular structure. It is appreciated that at least one of the ring-shaped elements may be truncated to provide a bending bias. The truncated elements may comprise of alternating flexible ring-shaped elements and rigid ring-shaped elements. In yet another aspect of the invention, the ring-shaped elements may vary in diameter and/or composition in different portions or sections of the tubular structure. In another aspect of the invention, some of the ring-shaped elements may be radiopaque, or the ring-shaped elements may comprise of different colors to operate as indicators along the tubular structure. Applications of the medical tubing of the invention include AV introducers, urological sheaths, ureteral access sheaths, urethral and bladder access sheaths, kidney access sheaths, ureteral stents, trocar cannulas, suction/irrigation tubing, insufflation tubing, vacuum tubing, split so sheath introducers, tracheostomy tubes, intubation tubes, gastronomy tubes, jujenostomy tubes, extracorporeal retrograde cholangeopancreatography catheters, endoscope shafts, drainage tubes, guide catheters, hydrocephalic shunts, guidewires, angioplasty and dilation balloons, vascular grafts, cholangiography catheters, vascular embolectomy/thrombectomy catheters, and central venous catheters.

In another aspect of the invention, a method of manufacturing the medical tubing having a length with variable characteristics is disclosed, the method comprising the steps of placing a plurality of ring-shaped elements upon a support member or mandrel in a series arrangement, and heating the plurality of ring-shaped elements to fuse them together over the support member or mandrel. The method of the invention may further comprise the step of placing the plurality of ring-shaped elements upon a second support member or mandrel before the heating step to subsequently form a second lumen or control tube to the tubular structure. This method may further comprise the step of forming a control tube over the assembled ring-shaped elements prior to the heating step. The control tube may comprise at least one of glass, silicone, heat shrinkable polyolefin, PTFE, FEP, metallic or other tubing that has a higher melting temperature than the assembled ring-shaped elements. This method may further comprise the step of coating the tubular structure with an elastomeric adhesive or dispersion. In another aspect of the invention, the mandrel may have a pre-formed curvature for accessing a specific region of a body cavity, the mandrel may include a collapsible, inflatable or dissolvable mandrel allowing the tubular structure to vary in diameter and lumen size, and the mandrel may be formed of an electrically dissolvable epoxy resin.

In another aspect of the invention, a method of manufacturing a medical tubing having a length with variable characteristics is disclosed, the method comprising the steps of placing a plurality of ring-shaped elements upon a support member or mandrel in a series arrangement, and fusing the plurality of ring-shaped elements together over the support member or mandrel with a solvent or other chemical compound. In this method of the invention, the fusing step may further comprise the step of immersing the ring-shaped elements into the solvent to fuse the elements.

In another aspect of the invention, a method of manufacturing a medical tubing having a length with variable characteristics is disclosed, the method comprising the steps of placing a plurality of ring-shaped elements upon a support member or mandrel in a series arrangement, and bonding together the plurality of ring-shaped elements upon a support member or mandrel with an adhesive. The adhesive may be photodynamic or heat-activated.

In another aspect of the invention, a method of manufacturing a thin-walled tube is disclosed comprising the steps of coating a wire with a plastic material, wrapping the coated wire around a mandrel forming a plurality of windings, and heating the wound coated wire until the plastic material melts and bonds the windings forming a wire-reinforced tube. In this method of the invention, the plastic material may comprise at least one of polyurethane, a thermoplastic material and a thermoset material. In another aspect of the invention, the wire may comprise at least one of a metallic material and a second plastic material, or the wire may be coated with the plastic material in a coextrusion process. This method of the invention may further comprise the step of compressing the windings as the coated wire is being heated.

In another aspect of the invention, this method may further comprise the step of providing a mold to compress the windings. This method may further comprise the step of removing the wire-reinforced tube from the mandrel after the tube is cooled. The wound-coated tube may also be heated until the plastic material is formed above, below and between all the windings. This method may further comprise the step of dipping the tube in a solvent-based solution forming an outer layer of the tube. In other aspects of the invention, the mandrel may be tapered to provide the tube with varying diameter throughout the length of the tube, the coated wire may be alternatively wound with the filament around the mandrel, the mandrel may be any shape such that the resultant shape of the tube may be removed from the mandrel after the heating step, and the mandrel may be a multiple-part mandrel.

In another aspect of the invention, a method of manufacturing a kink-resistant thin-walled tube having a length with different characteristics is disclosed, the method comprising the steps of coating a mandrel with a first layer of plastic material, placing a spring reinforcement over the first layer, and coating the spring reinforcement with a second layer of plastic material to form a spring-reinforced tube. In this method of the invention, each of the first layer and the second layer may be formed in either an extrusion process or a molding process. The spring reinforcement of the invention may be a pre-wound wire comprising at least one of a metallic material and a second plastic material. The method of the invention may further comprise the step of dipping the tube in a solvent-based solution forming an outer layer of the tube.

In another aspect of the invention, another method of manufacturing a kink-resistant thin-walled tube having a length with different characteristics is disclosed, the method comprising the steps of coating a mandrel with a first layer of plastic material, placing a spring reinforcement over the first layer, and dipping the spring-reinforced first layer in a solvent based solution to form a second layer of the tube. In this method of the invention, the second layer is impervious, the mandrel may be tapered to provide the tube with varying diameter throughout the length of the tube, and the mandrel may be any shape such that the resultant shape of the tube may be removed from the mandrel.

DESCRIPTION OF THE DRAWINGS

FIG. 1 illustrates a perspective view of a length of medical tubing according to a first embodiment of the invention;

FIG. 2 illustrates a perspective view of a single plastic ring of the tubing of the invention to be arranged in a series;

FIG. 3 illustrates a perspective view of the medical tubing of the invention being formed according to a process of the invention;

DESCRIPTION OF PREFERRED EMBODIMENTS AND BEST MODE OF THE INVENTION

Figure 4:
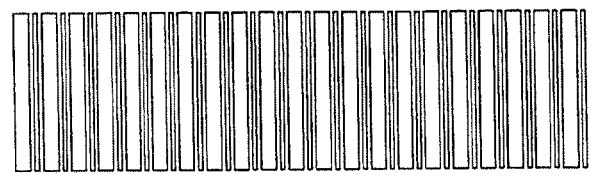
FIG. 4 is a side view of a composite tube of the invention in a straight condition.
Figure 6:
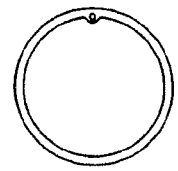
FIG. 6 is an end view of the composite tube of FIG. 4.

A medical tubing is illustrated in FIG. 1 and is designated by reference numeral 10. The medical tubing 10 is adapted for insertion into a body tissue or cavity. The tubing 10 has a proximal end 12, a distal end 14, a length and at least one lumen 15. The tubing 10 is constructed of a plurality of individual, discrete, generally ring-shaped elements 16 arranged in series to form a continuous tubular structure 18. FIG. 2 illustrates a perspective view of a single generally ring-shaped plastic ring 16 of the tubing 10 of the invention to be arranged in a series. In one aspect of the invention, the ring-shaped elements 16 are formed of a thermoplastic material. In another aspect of the invention, the ring-shaped elements 16 are formed of a thermoset material. The ring-shaped elements 16 may be arranged in series and subsequently fused or bonded by heat or chemical reaction to form a substantially continuous form.

Figure 5:
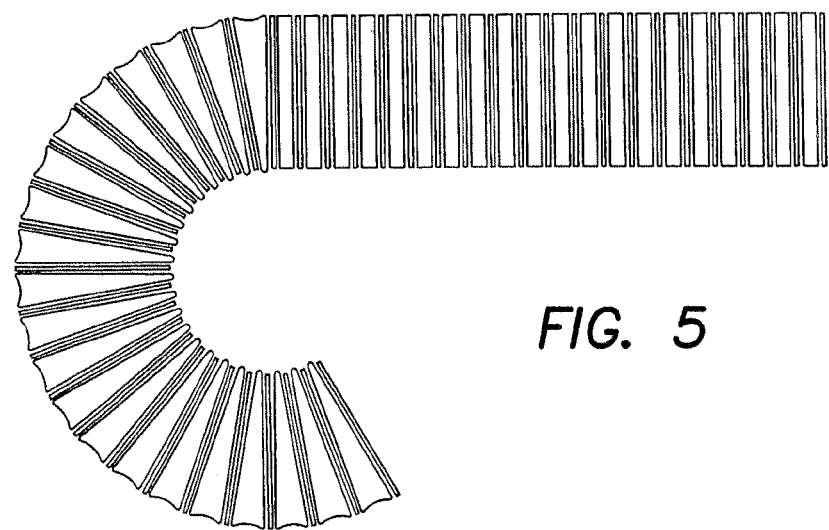
FIG. 5 is a side view of the composite tube of FIG. 4 in a bent condition.

Referring to FIG. 5, it can be seen that tubing constructed from a series of individual, discreet elements may be bent, shaped or coiled without kinking. In particular, the tubing 10 may have variable characteristics along the length. This may be achieved, for example, by the use of the ring-shaped elements 16 to provide different flexural modulus. For instance, a length of tubing may be constructed wherein flexible ring-shaped elements are separated by rigid ring-shaped elements, i.e., a flexible portion of a tubular structure may be formed adjacent to a rigid or semi-rigid portion of the tubular structure to provide variable flexibility. Such construction allows softer, more flexible material to be displaced and stretched along a curvature so that the rigid material is not deformed. A preferred embodiment may comprise a thermoplastic of a very rigid nature spaced by a compatible thermoplastic of a very soft nature. In other words, the ring-shaped elements 16 may be formed of two or more different materials having different chemical composition and hardness that are alternately fused or bonded together to form a continuous tube having circumferential portions that are alternately rigid and flexible.

Referring back to FIG. 3, there is shown a process of manufacturing the medical tubing 10 having variable characteristics of the invention where a support member or mandrel 20 is used to hold an assembly of ring-shaped elements 16 in an elongate, series arrangement. In particular, the process of manufacturing the medical tubing 10 comprises the steps of placing the plurality of ring-shaped elements 16 upon the support member or mandrel 20 in a series arrangement; and heating the plurality of ring-shaped elements 16 to fuse them together over the support member or mandrel 20. Additional lumens may be incorporated into the formed tubular structure 18 and supporting them with, e.g., an elongate wire. The arranged or assembled ring-shaped elements 16 are then heated so that the ring-shaped elements 16 are fused together over the mandrel(s) 20.

In another aspect of the invention, it is contemplated that a control tube is placed over the arranged or assembled ring-shaped elements 16 prior to the application of heat. The control tube may comprise of glass, silicone, heat shrinkable polyolefin, PTFE, FEP, metallic or other tubing that has a higher melting temperature than the assembled ring-shaped elements 16. A silicone control tube may be placed over the assembled ring-shaped elements 16 as the control tube and the assembled ring-shaped elements 16 are placed in an oven until the plastic ring-shaped elements 16 have fused together. Alternatively, the mandrel 20 may be heated until the thermoplastic ring-shaped elements 16 have fused together. The control tube and the mandrel(s) 20 are subsequently removed from the tubing 10.

In another aspect of the invention, the ring-shaped elements 16 could have either an inner diameter or an outer diameter or a combination of both comprising of thermoplastic or applied thermoset material along with the mandrel 20. A compression sleeve of silicone tubing could be placed over the structure and either heated or allowed to cure. The resulting product once the compression sleeve is removed would be very flexible and malleable and yet would have tremendous column strength. This structure and variants thereof would be applicable, e.g., to the malleable shaft graspers. In another aspect, the nested springs could be replaced with U-joints of various types.

Alternatively, the process of the invention could be accomplished with a thermoset material as follows. The spring wire is wound on the mandrel with the desired pitch. It is then coated in the thermoset such as silicone. Next, the silicone compression tube is placed over the spring wire and the assembly is allowed to cure. The tube is then removed from the silicone tube and mandrel. Springs can be pre-wound and can be made of materials other than steel that would otherwise not tolerate the heat required to flow a thermoplastic.

In another aspect of the invention, the entire process can be accomplished in the opposite manner to achieve the same results. This may be done by pre-winding a co-extruded wire into a spring and inserting it into a tube of desired diameter. A balloon or other such mechanism for pressurizing the spring coil may be inserted as the mandrel in the I.D. and the assembly are heated. As a result, the compression member is on the inside and the static member is on the outside.

It is appreciated that coating the mandrels with various types of low friction surfaces assist in the removal of the finished tube. For example, Teflon coatings and various mold releases have been found to be effective.

Multiple lumens can also be easily included in the fusing or bonding process of the invention. This can be accomplished in numerous ways. The first is to provide a groove in the winding mandrel and place a stainless tube in the groove. The winding extrusion is placed on the mandrel as before. When the resulting assembly is removed, the stainless tube will be imbedded in the plastic of the wire extrusion. Another way to accomplish multiple lumens is to wind separate mandrels with the wire extrusion and then instead of placing the silicone compression sleeve around each mandrel individually the mandrel assemblies are placed next to each other and the compression sleeve is placed over both of them. Mandrels can be of a variety of shapes to give the lumens of the resulting tube different internal and external shapes. Another version of this concept would be to assemble the mandrels with a strip or extrusion of plastic material (or non-plastic may work as well) in between the mandrels and then the assembled mandrels can have the extruded wire wound around them. The assembly would then be fused or bonded and the plastic in between the mandrels would form very thin walled lumens.

As such, it is appreciated that lumens can be placed external or internal to the main lumen of a catheter. Tremendous advantages in overall size of the catheters can be achieved because unlike conventional extrusion techniques which require that wall thickness be maintained constant, the catheters of the invention can have wall thickness not only of localized thickness increases but also lengths or sections of different materials.

The tubing constructed according to the present invention is especially unique in that it may be constructed having an extremely thin wall section. FIGS. 1-6 illustrate a relationship between a diameter of a tube and a wall thickness of that tube. Normally, tubing having a large diameter (0.200" or larger) and a very thin wall (0.015" or less) is extremely subject to kinking when it is bent, coiled or twisted. However, tubing constructed according to the present invention does not kink under the same circumstances since the softer materials allow bending without deformation of the primary, rigid material. It can be seen that as the tubing is bent, shaped or curved, the rigid material acts as a reinforcement to maintain the size and shape of the lumen whereas the soft material stretches along the large arc and compresses along the short arc. The stresses that normally accumulate along a thin walled tube and cause it to kink are absorbed and distributed in the composite construction of the present invention so that the tubing does not kink. Kink-free tubing may be constructed having wall thickness to diameter ratios in excess of 20:1, which in a standard extrusion is not possible. Wire coil reinforced tubing allows tubing to be made with a very thin wall. High diameter to wall ratios are possible when a wire coil is used to reinforce an extruded tube. However, wire reinforcement creates hysteresis and makes the formation of additional lumens problematic. In addition, it requires that formation of the tubing be done in a continuous form, not allowing for variations at specific regions along the length of the tubing.

In another embodiment of the invention, a method of manufacturing the medical tubing 10 having variable characteristics is disclosed, the method comprising the steps of placing the plurality of ring-shaped elements 16 upon the support member or mandrel 20 in a series arrangement; and fusing the plurality of ring-shaped elements 16 together over the support member or mandrel 20 with a solvent or other chemical compound. That is, this embodiment contemplates the use of solvent materials to fuse the various ring-shaped elements 16 together to form the continuous tubular structure 18. The ring-shaped elements 16 may be arranged or assembled upon the support member or mandrel 20 in a desired sequence for specific applications. Then, a solvent may be applied to the assembled elements so that they are fused together to form a continuous length of tubing. In another aspect of the invention, the assembled elements 16 may be immersed into a solvent to fuse the elements.

In yet another embodiment of the invention, an adhesive may be used to adhere the various ring-shaped elements 16 together to form the continuous tubular structure 18. For instance, a heat-activated adhesive may be formed as a ring-shaped element and placed between each of the rigid and flexible ring-shaped elements 16. When heat is applied, the adhesive is activated and the ring-shaped elements 16 are bonded. In another aspect, a photodynamic adhesive may be used to bond the ring-shaped elements 16. Such adhesives include epoxies that are cured by application of UV light. Other adhesives, such as cyanoacrylates and various rubber cements may be used to achieve specific results. Another aspect of the invention contemplates the use of a highly resilient, flexible rubber-like adhesive, such as silicone or other elastomeric adhesive, to bond the rigid ring-shaped elements 16 together. Such a construction allows the bond to absorb and distribute the forces that would normally kink a large-diameter, thin-walled tube and maintain the shape of the lumen. For instance, a series of rigid ring-shaped elements may be loosely assembled upon a mandrel or form and subsequently coated with an elastomeric adhesive or dispersion. The elastomeric adhesive material that flows between the rigid ring-shaped elements forms a resilient, flexible region between the rigid elements. An alternate embodiment contemplates the use of metallic rings assembled upon a mandrel and subsequently bonded together with a resilient, flexible elastomeric adhesive. The bending characteristics of such a construction may be imparted by varying the length of the metallic ring-shaped elements. For instance, a semi-rigid portion may be comprised of metallic ring-shaped elements that are long in comparison to the metallic ring-shaped elements of a flexible portion. The metallic ring-shaped elements of the flexible portion are shorter allowing a tighter or smaller bending radius.

The tubing and process of manufacturing of the tubing of the invention provide a distinct advantage over extrusion in that a sensitive flexible portion may be reinforced while less sensitive regions may be left alone or un-reinforced. Additionally, there are many medical applications where only a portion of the tubing should be flexible while other portions should be rigid or semi-rigid. There are also applications where a portion must be very soft and flexible but must also be non-compressible and kink-free and yet have a portion rigid enough to allow navigation through tortuous lumens. An example of conflicting requirements include endoscope shafts, urinary, billiary and vascular catheters as further described below. Many of these devices could benefit from a thin-walled tube that has a large primary lumen, one or more secondary lumens and a very flexible portion that may be controlled by pull wire(s) or cable(s) within the secondary lumen(s).

Figure 7:
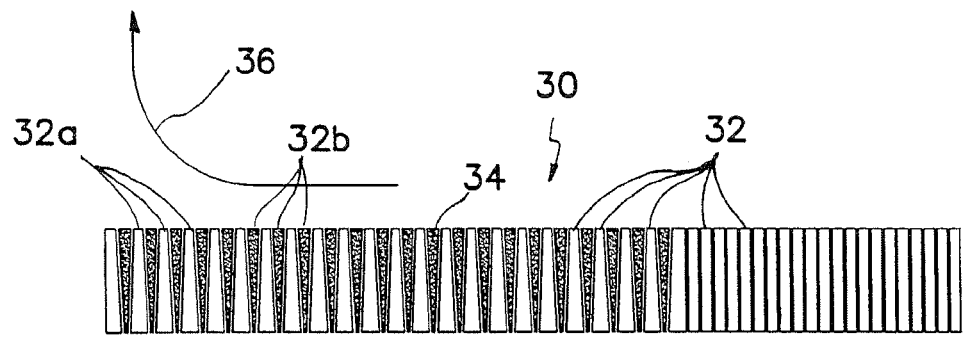
FIG. 7 is a side view of a tube having a bending bias in accordance with another embodiment of the invention.
Figure 8:
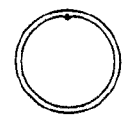
FIG. 8 is an end view of the tube of FIG. 7 having a bending bias.
Figure 9:
FIG. 9 is a side view of a wire-ring reinforced tube in a straight condition in accordance with another embodiment of the invention.
Figure 10:
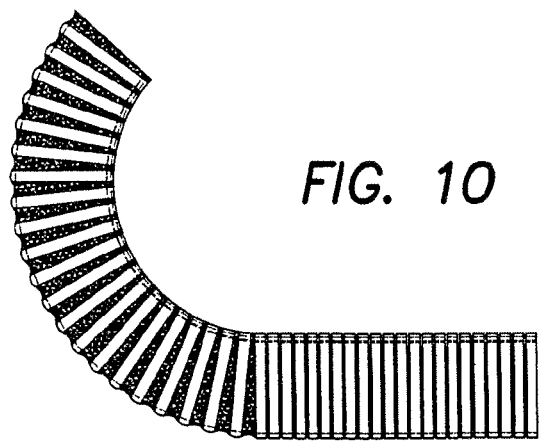
FIG. 10 is a side view of the wire-ring reinforced tube of FIG. 9 in a bent or circular condition.
Figure 11:
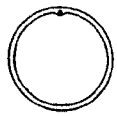
FIG. 11 is an end view of the wire-ring reinforced tube of FIG. 9.

Referring to FIG. 7, there is shown a length of tubing 30 according to another embodiment of the invention having alternating ring-shaped elements 32 that are shaped to provide a preferred bending bias 36. In this embodiment, the more rigid ring-shaped elements 32a are truncated or wedge-shaped, as are the less rigid elements 32b. A preferred arrangement of alternating truncated or wedge-shaped elements 32a and 32b provides the preferred bending bias 36. Stated another way, the larger flexible portion adjacent to the smaller rigid portion and is opposed to the smaller flexible portion adjacent to the larger rigid portion provides a bias toward the side having the larger flexible portion when a compression load is applied. The opposite is the case when a tension load is applied. As can be seen from the figures, the biasing arrangement may be formed adjacent to a rigid or semi-rigid arrangement of discreet, individual ring-shaped elements. FIG. 8 illustrates an end view of the tube having the bending bias of FIG. 7. FIGS. 9 and 10 are side views of a wire-ring reinforced tube in a straight and in a bent condition, respectively, in accordance with another embodiment of the invention, and FIG. 11 is an end view of the wire-ring reinforced tube of FIG. 9.

Figure 12A:
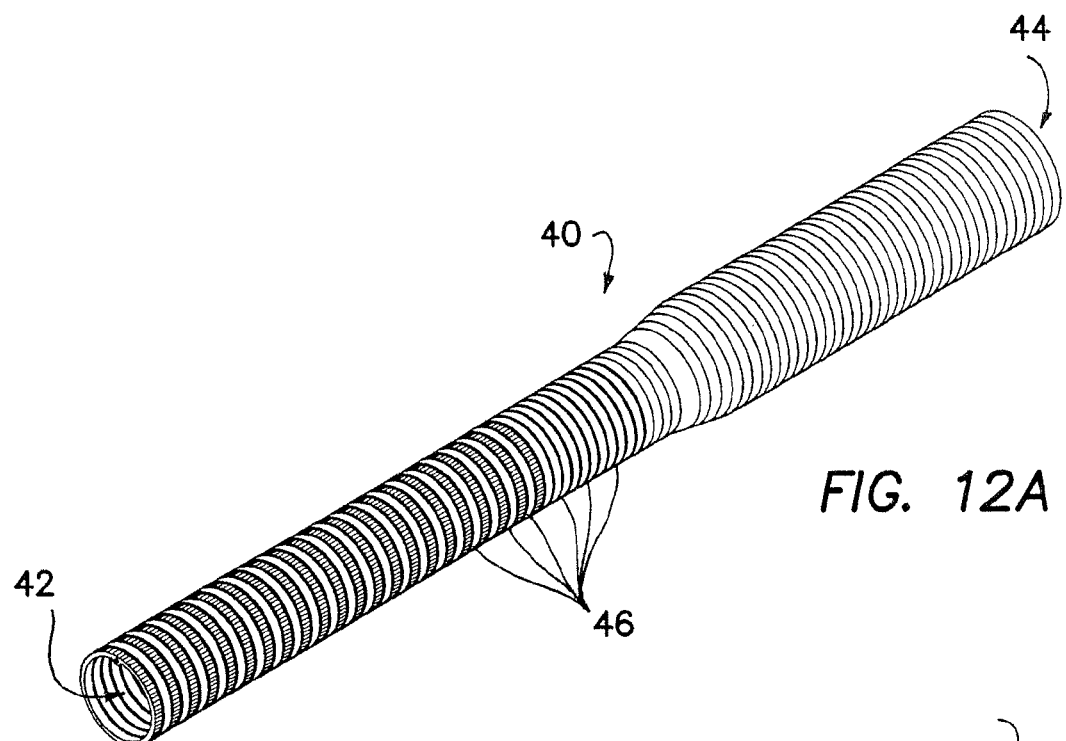
FIGS. 12(*a*) and 12(*b*) illustrate perspective views of tubes having varying diameters in accordance with additional embodiments of the invention.
Figure 12B:
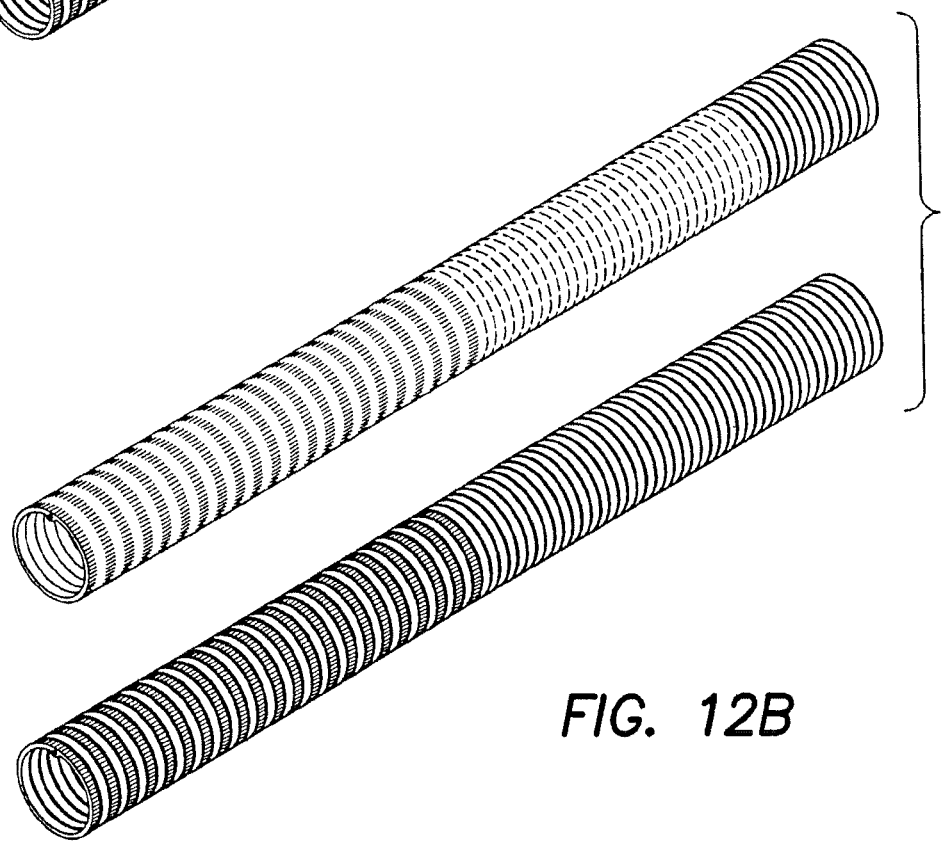

Referring to FIG. 12, a length of tubing 40 is shown having a first diameter 42 and at least a second diameter 44. The differing diameters are a product of assembling various ring-shaped elements 46 upon a forming mandrel and fusing the elements 46 together to form a continuous tube. It can be seen that many different arrangements of smaller, larger, softer and harder materials may be assembled in any number of ways. In addition, various colored elements may be arranged as indicators or radiopaque elements may be assembled along the length of the assembled tube. For example, a rigid portion of tubing may be produced for a specific length at a specific diameter, followed by a semi-rigid portion at a second diameter (smaller or larger), followed by a very flexible portion at a third diameter (smaller or larger), followed by a rigid or semi-rigid portion at a fourth diameter (smaller or larger) and so on.

The present invention also contemplates the use of mandrels or forms that may have curves or other useful forms or shapes that fit various uses. For instance, guiding catheters may be constructed that have pre-formed curvatures for accessing specific anatomical regions of a body. Mandrels or forms may include collapsible, inflatable, dissolvable or the like that allow the tubular body to have variations in diameter and lumen size. As an example, a mandrel or form may be constructed of an electrically dissolvable epoxy resin. The mandrel or form retains its shape until an electrical impulse is applied. The material separates upon application of electrical energy leaving a complex lumen shape within the tubular body.

The following is yet another example of a process for making thin-walled tubes of the invention:

(1) First, a mandrel of steel is machined to match the internal diameter or shape of the intended tube;

(2) Second, a stainless steel wire, e.g., of about 0.006" in diameter has a layer of polyurethane co-extruded onto it with a resulting diameter of about 0.020";

(3) The co-extruded wire is close wound around the length of the mandrel and the ends are secured such that the resultant coil will not unwind;

(4) Fourth, a silicone tube with an inner diameter (I.D.) less than that of the wound coil outer diameter (O.D.) is placed over the entire assembly such that it completely covers the wound coil;

(5) Fifth, the assembly is placed in an oven at approximately 180° C. for 15 to 30 minutes (this is for Pellethane; other plastics require different parameters.);

(6) Sixth, the assembly is removed from the oven and cooled. The silicone sheath is removed once the assembly has cooled; and (7) Seventh, the wound coil is removed from the mandrel.

This process results in a tube with walls of about 0.015" in thickness and a reinforced coil of stainless wire embedded in it. The tube is virtually un-kinkable and has very smooth inner and outer diameter surfaces. In addition, the mandrel can be tapered to provide a tube with variable diameters from one end to the other. In other examples, physical properties of the resulting tube can be adjusted by varying the diameter of the wire, the diameter of the co-extruded plastic, the type and properties of the wire and plastic such as chemical composition and hardness. The tolerance that can be held on the I.D. of the tube is very high and on the order of 0.001" or less. The tolerance on the O.D. is comparable. The range of diameters for this process is quite large. Prototypes have been made from 0.026" I.D. to 0.75" I.D. and with wires from 0.004" diameter to 0.008" inch diameter.

It should be noted that two or more different types of wire/plastic extrusions can be wound together and the wire is not a requirement for this process to work. This process would be useful for molding thin wall tubes to dimensions that are not practical or obtainable by extrusion or traditional molding. Mandrels do not need to be round and could combine both round and non-round shapes on the same mandrel.

The main requirement is that the resultant shape be capable of being removed from the mandrel once the heat cycle is finished. With unusual shapes this could be accomplished with split mandrels and sacrificial mandrels that could be removed by dissolving in acid by way of example.

The method of the invention may be applied in the construction of the following products, at least in part if not in whole:

1. AV introducers: These devices are used to gain access to blood vessels. The AV introducers of the prior art are typically fairly thick walled fluoropolymer about 2-3 inches long. The AV introducers of the invention decrease wall thickness and at the same time increase kink resistance. Vascular surgeons also use longer versions of these to access various parts of the vascular system and then use these sheaths to inject various medicants or use them as a highway for the introduction and removal of instruments. These longer versions can be 70 centimeters in length or more and would benefit tremendously by the increased kink resistance and flexibility that the AV introducers of the invention would offer. More specifically, the sheath of the invention would be capable of being coated internally as well as externally with friction reducing coatings such as hydrophilic coatings as well as heperanized coatings or other medically beneficial surface treatment.

2. Urological sheaths: Different urological sheaths can be produced by the methods of the present invention, e.g., ureteral access sheaths, urethral and bladder access sheaths, and kidney access sheaths modified to direct a scope for various procedures.

3. Ureteral stents: These can be made with the process of the invention and would have the benefits of thin walls, high column strength and tremendous flexibility. The common wisdom in urology is that thin flexible stents are more comfortable for the patient but more difficult for the physician to place. Larger more rigid stents are easier to place but uncomfortable for the patient. The stent of the invention would be both small and flexible and yet easy to place due to its inherent column strength.

4. Trocar cannula: These can be made to be very thin walled and yet flexible (or inflexible), and can be very resistant to kinking or compressing. This may be achieved by the bonding or fusing process of the invention with a braided structure instead of a coil. In another aspect, a folded structure could be made that would allow the cannula sheath to be inserted first followed by the cannula itself.

5. Suction/Irrigation (S/I) tubing: Prior art S/I tubing is currently made from PVC and is very thick walled to prevent the tube from kinking or collapsing under vacuum. With the process of the invention, the following benefits can be achieved—the tubing would be kink resistant yet have thin walls and therefore be lightweight, cost would be comparable to PVC without the environmental concern, thus, it would reduce the overall amount of plastic used. Currently, S/I tubes have 1 to 2 lbs of PVC tubing in them. The S/I tubing of the invention would reduce the overall weight of plastic to approximately 1/10 of a pound and would be easier for the surgeon to use. In addition, the wire in the irrigation tube could be electrically heated to allow the fluid to be at or near body temperature when introduced to the patient.

6. Insufflation tubing: This tubing is used to deliver carbon dioxide gas for laparoscopic surgery and has some of the same problems as S/I tubing. Lighter weight and less plastic wasteful tubing could be made, and the heating element in the wall would be of benefit to the patient by allowing body temperature gas to be introduced instead of colder gas.

7. Vacuum tube: The process of the invention would be beneficial to any situation, either medical or non-medical, where the need exists for a vacuum tube to be thin walled and preferably kink resistant. This process could also be used to produce thin walled pressure tubes.

8. Split sheath introducers: The process of the invention can be modified to make a split sheath introducer. The wire extrusion can be wound on a special mandrel to make a semicircular tube on each side of the mandrel and then fusing or bonding the split sheath together.

9. Tracheostomy tubes: Thin walled kink-free tracheostomy tubes would benefit from the process of the invention. The balloon-filled lumen could be easily fused or bonded together along with the breathing tube. The same advantages would apply to crycothyrodectomy tubes used in emergency situations.

10. Intubation tubes: The intubation tubes have very thin walls and are very kink resistant which would help enormously with these devices especially in pediatrics or cases where the trachea has become constricted. The flexibility would make them ideal for nasal tubes as well.

11. G-tubes/J-tubes: Gastronomy and jujenostomy tubes are used for enteral feeding and would likewise benefit from reduced diameters, enhanced column strength for insertion, and kink resistance for safety.

12. ERCP catheters: Extracoporeal retrograde cholangeopancreatography catheters are very long catheters typically used to treat gallstones in the cystic duct. These would benefit from the increased column strength and reduced wall thickness as well as high kink resistance.

13. Endoscope shafts: Flexible and steerable endoscopes require shafts that can give good protection to the internal components as well as provide regions of variable flexibility and good column stiffness throughout. The shafts must also accommodate multiple lumens.

14. Drainage tubes: Drainage and suction tubes would also benefit from thin walls, lightweight and kink resistance.

15. Guide catheters: Guide catheters commonly used in cardiology to gain access to the coronary arteries are carefully designed to meet various design criteria such as shape, stiffness, steerability, torque strength and kink resistance. They have to be smooth and non-thrombogenic. The bonding and fusing process of the invention can serve as a good basis of construction for these devices. Torque strength or torqability can be improved in devices of the invention by putting relatively stiff elements along the length of the shaft or by altering the plastic used to extrude over the wire.

16. Hydrocephalic shunts: A common problem with these shunts, which are used to drain excess hydrocephalic fluid from the ventricles of the brain, is that they can kink and prevent adequate drainage. This in turn can require a revision to be performed or merely patient discomfort and possibly increase the chances of an infection. By producing portions of them with the process of the invention, it is possible to create very crush as well as kink resistant shunts.

17. Guidewires: Guidewires are used in a number of applications including urology and radiology. They are commonly constructed with close wound stainless steel springs and then coated with Teflon or a plastic for lubricity. They are typically 2 to 6 feet long and are around 1 mm in diameter or less. These structures can be fabricated with the process of the invention.

18. Angioplasty and dilation balloons: The catheters that these balloons are placed on require the ability to transmit as much as 15 atmospheres or more over a 3-foot or longer length. Here again the advantages of reinforced thin walls with excellent column strength would be very helpful.

19. Vascular grafts: A variety of graft designs are commonly used and these include designs for aortic grafts, dialysis grafts, bypass grafts, arterial grafts for various locations in the peripheral vasculature. All of these will benefit from kink resistance and crush resistance as well as excellent flexibility. Various coatings and surface modifications can be applied.

20. Cholangiography catheters: Catheters used to deliver contrast media to the cystic duct are difficult to use as the conflicting requirements of kink resistance and thin walls make necessary a compromise. This is not the case with the tubing of the invention where the wall can be kept very thin and kink resistant.

21. Vascular embolectomy/thrombectomy catheters: These small diameter catheters have balloons on them for removing clots and in the case of thrombectomy they have a spring body which would make the process of the invention a natural for them. As for the embolectomy catheters, they may benefit from the educed profile, increased inflation lumen and guidewire lumens.

22. Central venous catheters: These catheters are placed near the clavicle and access the superior vena cava through one of the subclavian or innominate veins. They are used for emergency treatment in the case of kidney failure among other uses. These catheters are frequently constructed with two and three lumens and require the ability to extract and return blood quickly. They would benefit from the processes of the invention in that the walls can be made thinner for increased flow or reduced profile or both. They would be almost kink proof and they would have tremendous column strength which would aid in insertion. The processes of the invention would not interfere with any of the commonly used coatings and they may show up better on ultrasound.

The foregoing disclosure and description of the invention are illustrative and explanatory thereof, and various changes in the size, shape and materials, as well as in the details of the illustrated construction, may be made without departing from the spirit and scope of the invention. For these reasons, the above description should not be construed as limiting the invention, but should be interpreted as merely exemplary of preferred embodiments.

We claim:

1. A method of manufacturing a multi-lumen tube, comprising:
    coating a first wire with a plastic material;
    winding the coated first wire around a first mandrel, thereby forming a plurality of windings in a first wound coated wire;
    coating a second wire with a plastic material;
    winding the coated second wire around a second mandrel, thereby forming a plurality of windings in a second wound coated wire;
    placing a compression sleeve over the second wound coated wire and the first wound coated wire to compress the second wound coated wire against the first wound coated wire prior to heating; and
    heating the second wound coated wire and the first wound coated wire in the compression sleeve until the plastic material fuses the windings such that a second wire-reinforced tube is formed next to a first wire-reinforced tube as the multi-lumen tube.

2. The method of claim 1, further comprising removing the compression sleeve after heating the second wound coated wire along with the first wound coated wire.

3. The method of claim 1 wherein the wire-reinforced tube has a lumen and a diameter size different than a lumen and diameter size of the second wire-reinforced tube.

4. The method of claim 1, wherein the plastic material comprises at least one of polyurethane, a thermoplastic or a thermoset.

5. The method of claim 1, wherein at least one of the wires comprises at least one of a metallic material or a second plastic material.

6. The method of claim 1, wherein at least one of the wires is coated with the plastic material in a coextrusion process.

7. The method of claim 1, wherein at least one of the first wire-reinforced tube or the second wire-reinforced tube has a wall thickness of approximately 0.015 inches or less.

8. The method of claim 1, wherein at least one of the first wire-reinforced tube or the second wire-reinforced tube has an inner diameter that ranges from approximately 0.026 inches to approximately 0.75 inches.

9. The method of claim 8, wherein the tolerance on the inner diameter is on the order of approximately 0.001 inches or less.

10. The method of claim 1, wherein the heating is effected until the plastic material is formed above, below and between all the windings.

11. The method of claim 10 further comprising dipping the multi-lumen tube in a solvent-based solution forming an outer layer on the multi-lumen tube.

* * * * *